United States Patent [19]

Dubs et al.

[11] 4,011,233

[45] Mar. 8, 1977

[54] 2-METHYL-2-(4-METHYL-3-PENTENE-1-YL) THIAZOLIDINE

[75] Inventors: Paul Dubs, Zug; Heiner Küntzel, Oberengstringen; Mario Pesaro, Zurich; Harald Schmidt, Wallisellen, all of Switzerland

[73] Assignee: Givaudan Corporation, Clifton, N.J.

[22] Filed: Aug. 22, 1975

[21] Appl. No.: 606,808

Related U.S. Application Data

[62] Division of Ser. No. 374,714, June 28, 1973, Pat. No. 3,944,561.

[52] U.S. Cl. .......................... 260/306.7 R; 426/535
[51] Int. Cl.² ........................................ C07D 277/04
[58] Field of Search ............................ 260/306.7 R

[56] References Cited

UNITED STATES PATENTS

| | | | |
|---|---|---|---|
| 2,815,338 | 12/1957 | Ruegg | 260/306.7 R |
| 2,886,571 | 5/1959 | Schade et al. | 260/306.7 R |

FOREIGN PATENTS OR APPLICATIONS

| | | | |
|---|---|---|---|
| 345,343 | 4/1956 | Switzerland | 260/306.7 R |

OTHER PUBLICATIONS

Tondeur et al., Chemical Abstracts, vol. 62, (1965), p. 5264b.

*Primary Examiner*—Donald G. Daus
*Assistant Examiner*—David E. Wheeler
*Attorney, Agent, or Firm*—Thomas Cifelli, Jr.

[57] ABSTRACT

Novel thiazolidines, a process for their manufacture, and odorant and/or flavorant compositions containing the novel compounds are disclosed.

1 Claim, No Drawings

2-METHYL-2-(4-METHYL-3-PENTENE-1-YL) THIAZOLIDINE

This is a division of application Ser. No. 374,714 filed June 28, 1973, now U.S. Pat. No. 3,944,561.

FIELD OF THE INVENTION

This invention relates to the fields of odorants and/or fragrances.

SUMMARY OF THE INVENTION

The present invention relates to thiazolidines as odorant and/or flavoring substances. More particularly, the invention is concerned with odorant and/or flavoring compositions containing thiazolidines and with a method of imparting an odor and/or flavor to products using thiazolidines. The invention is also concerned with certain thiazolidines per se and a process for the manufacture thereof.

DESCRIPTION OF THE PREFERRED EMBODIMENTS

The odorant and/or flavoring compositions provided by the present invention contain as an essential odor- and/or flavor-imparting ingredient a thiazolidine of the general formula

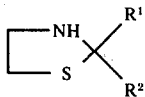
(I)

wherein
  $R^1$ represents a hydrogen atom and
  $R^2$ represents an aliphatic $C_{2-10}$ hydrocarbon group (other than a $C_{3-6}$ isoalkyl group), an aliphatic $C_{1-10}$ hydrocarbon group substituted by a group X, or a group $R^3$;
  $R^3$ represents an araliphatic $C_{7-10}$ hydrocarbon group, a 5- or 6- membered monocyclic, carbocyclic or heterocyclic aromatic group, a dioxolane group which may be sutstituted or a group —COOR$^4$,
  X represents an oxo group which may be ketalised or a group —COOR$^4$, —SR$^5$ or —OR$^5$;
  $R^4$ represents a $C_{1-6}$ alkyl group and
  $R^5$ represents a hydrogen atom or a $C_{1-6}$ alkyl or $C_{1-6}$ acyl group or
  $R^1$ and $R^2$ each independently represents an aliphatic $C_{1-10}$ hydrocarbon group, which may be substituted by a group X, or a group $R^3$ or
  $R^1$ and $R^2$ together represent a —(CH$_2$)$_{4-7}$ group.

Aliphatic $C_{2-10}$ hydrocarbon groups can be straight-chain or branched-chain, unsaturated, preferably mono-olefinically unsaturated, or saturated groups. $C_{3-6}$ isoalkyl groups are the isopropyl, isobutyl, isopentyl and isohexyl groups. Examples of araliphatic $C_{7-10}$ hydrocarbon groups are the benzyl and phenethyl groups. Examples of 5- or 6-membered monocyclic, carbocyclic or heterocyclic aromatic groups are the phenyl, furyl, pyrrolyl, thienyl, imidazolyl, thiazolyl, pyridyl and pyrazyl groups. An example of a dioxolane group which may be substituted is the 2,2-dimethyl-4-dioxolanyl group. A $C_{1-6}$ acyl group is preferably derived from an aliphatic monocarboxylic acid such as formic acid, acetic acid or propionic acid. Examples of ketalised oxo groups are the dimethoxy, diethoxy, methylenedioxy, ethylenedioxy and phenylenedioxy groups.

Examples of thiazolidines of formula I in which $R^1$ represents a hydrogen atom are 2-ethyl-, 2-propyl-, 2-butyl-, 2-secbutyl-, 2-pentyl-, 2-hexyl-, 2-heptyl-, 2-(2-methylthioethyl)-, 2-ethoxycarbonyl-, 2-hydroxymethyl-, 2-phenyl-, 2-benzyl-, 2-(2-furyl)- and 2-(2-pyrrolyl)-thiazolidine. Examples of thiazolidines of formula I in which $R^1$ and $R^2$ each independently represent an aliphatic $C_{1-10}$ hydrocarbon group, which may be substituted by a group X, or a group $R^3$ or in which $R^1$ and $R^2$ together represent a —(CH$_2$)$_{4-7}$ group are 2-methyl-2-(4-methyl-3-penten-1-yl)-, 2-acetyl-2-methyl-, 2-methyl-2-isopropyl-, 2-(1-hydroxyethyl)-2-methyl-, 2-hydroxymethyl-2-methyl-, 2-ethoxycarbonyl-2-methyl-, 2,2-dimethyl-, 2,2-dipropyl-, 2-ethyl-2-methyl-, 2-hexyl-2-methyl-, 2,2-tetramethylene- and 2,2-pentamethylene-thiazolidine.

A group of novel thiazolidines which are subgeneric to the compounds of formula I referred to earlier, and which also form part of this invention, can be generically formulated thus:

(II)

wherein
  $R^6$ represents a hydrogen atom or the methyl, ethyl, ethoxycarbonyl, ethoxycarbonylmethyl or acetoxymethyl group and
  $R^7$ represents the butyl, secbutyl, pentyl, decyl, 4-methyl-3-pentenyl, dimethoxymethyl, 2-methylthioethyl, 2-furyl, 2-(5-methylfuryl), 2-thienyl, 2-(5-methylthienyl), 2-pyrrolyl, 2-(N-methylpyrrolyl), pyridyl or 4-(2,2-dimethyldioxolanyl) group when $R^6$ represents a hydrogen atom; or represents the isopropyl, isobutyl, 4-methyl-3-pentenyl, 1-hydroxyethyl, acetyl, propionyl, acetoxymethyl, 2-(1-acetoxyethyl), 3-hydroxypropyl or 2,2-dimethoxyethyl group when $R^6$ represents the methyl group; or represents the butyl or acetyl group when $R^6$ represents the ethyl group; or represents the ethoxycarbonyl or 1-ethoxycarbonyl-ethyl group when $R^6$ represents the ethoxycarbonyl group; or represents the ethoxycarbonyl-methyl group when $R^6$ represents the ethoxycarbonylmethyl group; or represents the acetoxymethyl group when $R^6$ represents the acetoxymethyl group.

The thiazolidines of formula I or formula II can be manufactured according to known procedures; for example, by condensing cysteamine with a keto compound of the formula $R^1$—CO—$R^2$ or $R^6$—CO—$R^7$. The condensation can be carried out in the presence of, or in the absence of, a solvent. Suitable solvents include water, alcohols such as methanol, ethanol etc, ethers such as diethyl ether, dioxan, tetrahydrofuran etc, hydrocarbons such as benzene, toluene etc, halogenated hydrocarbons such as methylene chloride, chloroform etc, amides such as dimethylformamide etc. Preferred solvents are methanol and ethanol (method A hereinafter) or benzene (method B hereinafter), the condensation proceeding particularly well in the latter case with azeotropic removal of the water which is formed. The molar proportion of cysteamine to keto compound conveniently amounts to 1:1, although one or both condensation components can be employed in excess. Cysteamine can be used as such or in the form of an ammonium salt with an organic or inorganic acid. In the latter case, cysteamine can be liberated in situ by means of a base. It can also be generated in situ from suitable precursors (e.g. from ethyleneimine with hydrogen sulphide).

The keto component can be used as such or in protected form (e.g. as the acetal or ketal), in the latter case the condensation conditions being chosen so that the free keto compound is formed in situ. The condensation is conveniently carried out at a temperature between 0° C and 150° C, preferably between room temperature and the boiling temperature of the solvent used. The duration of the condensation amounts to between about 5 minutes and 24 hours depending on the temperature and reactivity of the keto compound used. The condensation is advantageously carried out in an inert gas atmosphere (e.g. nitrogen or argon).

The isolation of the condensation product can be carried out according to known methods; for example, by concentrating the solution, taking up the residue in an organic extraction agent, washing and drying the organic phase and distillation or by filtering the concentrated solution through aluminium oxide and subsequent distillation.

The thiazolidines of formula I are distinguished by particular fragrance and flavour qualities, different notes in the foreground appearing according to the nature of the substituents in the 2-position. The aroma spectrum of the thiazolidines of formula I can extend from ester like-fruit like, green, mushroom- and vegetable-like (bean, asparagus, onion, radish), through nutty, butter-like, fatty, caramellous to smoky, spicy, meaty or fish like.

The thiazolidines of formula I can accordingly be used for the aromatization of foodstuffs such as soups, vegetables, sauces etc. The pronounced flavour qualities of the thiazolidines enable them to be used in finished products in small concentrations (e.g. in the range of 0.01–10 ppm, preferably 0.1–1 ppm).

The thiazolidines of formula I can be mixed with usual carrier materials and/or diluents, if desired with other flavour-imparting ingredients and if necessary with emulsifiers, to form aromatizing agents which confer to foodstuffs, for example, a spicy or a vegetable flavour or which intensify such a flavour. The thiazolidines of formula I can, however, also be added alone to the products to be aromatized. In this case, particular attention must be paid, when carrying out the addition, to providing a homogeneous distribution of the thiazolidine in the product to be aromatized. Where the thiazolidines are used as components for the manufacture of artificial aromas, these aromas can be formulated, for example, as liquids, pastes or powders. The products can, for example, be spray-dried, vacuum-dried or lyophilized. The formulation of such artificial aromas as well as the aromatiziation of foodstuffs can be carried out in a manner which is known per se [see J. Merory; Food flavourings, composition, manufacture and use; Avi Publ. Co. Inc. Westport (1968)].

The following Examples illustrate the manner in which the thiazolidines aforesaid can be prepared:

Method A:

EXAMPLE 1

37.0 g (0.2 mol) of 6-methyl-hepten-(5)-one-(2) were dissolved in 50 ml of ethanol and treated under an inert gas atmosphere with a solution of 15.43 g (0.2 mol) of cysteamine in 500 ml of ethanol. The mixture was heated for 2 hours under reflux to 100° C. The solution was then concentrated on a rotary evaporator and the residue subjected to a fractional distillation (Widmer column) under a high vacuum. There were obtained 27.38 g (yield 74% of theory) of 2-methyl-2-(4-methyl-3-penten-1-yl)-thiazolidine of boiling point 74°–76° C; $n_D^{20} = 1.5150$. IR: $\nu_{max} = 1445, 1378, 790$ cm$^{-1}$. Odour: green, sulphurous; flavour: green, aldehyde-like.

EXAMPLE 2

4.3 g (0.05 mol) of diacetyl were added under an argon atmosphere to a solution of 3.85 g (0.05 mol) of cysteamine in 40 ml of methanol, whereby a warming of the mixture was observed. Thereafter, the mixture was heated to boiling under an argon atmosphere for 30 minutes. The solvent was removed on a rotary evaporator and the gas-chromatographically uniform crude product was subjected to short-path distillation in a bulb tube. There were thereby obtained 6 g (yield 83% of theory) of gas-chromatographically uniform 2-acetyl-2-methyl-thiazolidine of boiling point $_{0.03}$ 65° C; $n_D^{20} = 1.5217$. IR: $\nu_{max} = 1710, 1430, 1360, 1155, 1075, 855, 790$ cm$^{-1}$. Odour: buttery, caramellous note, nutty, reminiscent of biscuit; flavour; diacetyl-like in the direction of caramel-butter, faintly nutty.

Method B:

EXAMPLE 3

15.43 g (0.2 mol) of cysteamine and 29.0 g (0.2 mol) of isopropyl methyl ketone were treated with 200 ml of benzene and boiled under an inert gas atmosphere for 14 hours on a water-separator. The solution was concentrated on a rotary evaporator and filtered over 25 g of neutral aluminium oxide (activity I). The aluminium oxide was then flushed with ether. The filtrate was again concentrated and subsequently distilled under a high vacuum through a Widmer column. 22.51 g (yield 77% of theory) of 2-isopropyl-2-methyl-thiazolidine ($n_D^{20} = 1.5085$) passed over in a boiling range of 40°–42° C and at a pressure of 0.009 mm Hg. IR: $\nu_{max} = 1440, 1370, 790$ cm$^{-1}$. Odour: camphorous, woody; flavour: greenish.

EXAMPLE 4

In an analogous manner to that described in the previous Examples, the thiazolidines listed in the following Table can be manufactured:

Table

| Thiazolidine | B.p./mm Hg | $n_D^{20}$ | Yield | IR (cm$^{-1}$) | Olfactory interpretation |
|---|---|---|---|---|---|
| 2-(1-Hydroxyethyl)-2-methyl-thiazolidine | 58°–62° C/0.05 M.p. 35°–40° C | — | 67% | 1450, 1370, 1105, 805 | Odour: burnt, caramellous. Flavour: buttery-fatty, faint burnt note. |
| 2-Acetyl-2-ethyl-thiazolidine/2-methyl-2- | 62°–64° C/0.04 | 1.515 | 41% | 1715, 1435, 1378, 850 | Odour: burnt, meaty. |

Table-continued

| Thiazolidine | B.p./mm Hg | $n_D^{20}$ | Yield | IR (cm$^{-1}$) | Olfactory interpretation |
|---|---|---|---|---|---|
| propionyl-thiazolidine | | | | | Flavour: nutty, meaty. |
| 2-Ethyl-2-butyl-thiazolidine | 45°–48° C/0.04 | 1.5009 | 34% | 1455, 1378, 830 | Odour: pyrazine-like, milk-like, caramellous. Flavour: weakly minty, (spearmint) weakly nutty. |
| 2-Isobutyl-2-methyl-thiazolidine | 50°–53° C/0.009 | 1.5010 | 58% | 1465, 1375, 770 | Odour: green, flowery, sweetish. Flavour: greenish, ester-like, fruity. |
| 2-Secbutyl-thiazolidine | 60° C/0.04 | 1.5059 | 75% | 1460, 1380, 1190, 830 | Odour: green, fruity, pyridine-like. Flavour: weakly roasted, somewhat nut-like. |
| 2-(2-methylthioethyl)-thiazolidine | 85° C/0.04 | 1.5645 | 69% | 1440, 930, 830 | Odour: potato-like, slightly roasted. Flavour: potato-like, slightly fatty. |
| 2-Butyl-thiazolidine | 60° C/0.08 | 1.5031 | 63% | 1455, 1185, 825, 790 | Odour: green-penetrating, bean-like, somewhat sulphurous note. Flavour: greenish, earthy, towards green tomatoes, raw potatoes. |
| 2-Pentyl-thiazolidine | 60° C/0.08 | 1.5002 | 83% | 1455, 1190, 855, 810 | Odour: greenish, spicy-earthy, vegetable-like towards beans, asparagus, tomato). Flavour: strongly green, somewhat fatty, cucumber-like, towards asparagus or tomato. |
| 2-(2-Furyl)-thiazolidine | M.p. 51.5°–58.5° C | — | 84% | 1450, 1160, 1115, 930, 840, 815 | Odour: smoky, spicy, meaty, salami-like. Flavour: mushroom-like, earthy. |
| 2-(2-Pyrrolyl)-thiazolidine | M.p. 110°–111° C | — | 72% | 1455, 1440, 1190, 1100, 1030, 915, 885, 825 | Flavour: weakly flowery, somewhat nut-like and coffee-like. |
| 2-Hydroxymethyl-2-methyl-thiazolidine | M.p. 38°–45° C | — | 55% | 1455, 1375, 1075, 805 | Odour: meaty, bread-like, hazel-nut like. Flavour: nutty, meaty. |
| 2-Ethoxycarbonyl-2-methyl-thiazolidine | 93°–96° C/0.04 | 1.4985 | 67% | 1730, 1440, 1180, 835 | Odour: spicy, greenish-fruity. Flavour: fruity, caramellous, sweetish, woody. |
| 2-Ethoxycarbonyl-thiazolidine | M.p. 27°–29° C | — | 90% | 1740, 1450, 1295, 820 | Odour: fruity, smoky, pyrazine-like. Flavour: weakly fruity, woody trace, somewhat smoky. |
| 2-Hydroxymethyl-thiazolidine | 105° C/0.04 M.p. 47°–48° C | — | 37% | 1462, 1380, 1065, 950 | Odour: green, woody, roasted, spicy. Flavour: greenish, somewhat bitter. |
| 2,2-Tetramethylene-thiazolidine | 48°–50° C/0.04 | 1.5409 | 57% | 1440, 1325, 810 | Odour: greenish, fishy, meaty. Flavour: roasted, fishy, meaty. |
| 2,2-Pentamethylene-thiazolidine | 57°–60° C/0.04 M.p. 29°–31° C | — | 76% | 1445, 882, 798 | Odour: pyrazine-like, smoky, nutty. Flavour: earthy, nutty, broth-like. |
| 2-Methyl-2-propyl-thiazolidine | 35°–36° C/0.04 | 1.5040 | 67% | 1460, 1375, 790 | Odour: woody, fruity, nutty-fatty. Flavour: onion-like, fruity. |
| 2-Methyl-2-pentyl-thiazolidine | 74°–75° C/0.04 | 1.4979 | 60% | 1460, 1375, 790 | Odour: green, flowery, sweet. Flavour: flowery, sweet, greenish. |
| 2-Hexyl-2-methyl-thiazolidine | 79°–81° C/0.04 | 1.4955 | 60% | 1460, 1375, 800 | Odour: cocoa-like, fatty, fruity. Flavour: fatty-waxy, cocoa-like trace. |
| 2,2-Dipropyl-thiazolidine | 60°–62° C/0.04 | 1.4991 | 29% | 1460, 1380, 795 | Odour: pyrazine-like, ester-like, green, slight caramel note. Flavour: greenish sulphurous. |
| 2-Butyl-2-methyl-thiazolidine | 43°–45° C/0.04 | 1.5021 | 37% | 1460, 1375, 805, 785 | Odour: ester-like, milk-like, green, slightly burnt Flavour: caramellous, nutty. |
| 2-Heptyl-thiazolidine | 79°–81° C/0.04 | 1.4959 | 72% | 1460, 1380, 840, 805 | Odour: ester-like, green, bean-pod like, ivy, slightly flowery. Flavour: aldehydic-fatty, greenish-flowery. |
| 2-Octyl-thiazolidine | 98°–99° C/0.04 | 1.4938 | 71% | 1460, 1380, | Odour: pyrazine-like, |

Table-continued

| Thiazolidine | B.p./mm Hg | $n_D^{20}$ | Yield | IR (cm$^{-1}$) | Olfactory interpretation |
|---|---|---|---|---|---|
| | | | | 810 | meaty, roasted. Flavour: strong aldehydic-fatty, metallic. |
| 2,2-Diethyl-thiazolidine | 37° C/0.01 | 1.5086 | 75% | 1460, 1375, 835 | Odour: meaty, fishy, sardine-like, slightly fatty. Flavour: solvent-like (acetone). |
| 2-Benzyl-thiazolidine | 80° C/0.06 M.p. 33.5°–34.5° C | — | 38% | 1605, 1500, 1460, 1190, 1120, 805, 760, 705 | Odour: greenish, flowery, slightly phenylacetaldehyde-like. Flavour: sweet, flowery such as phenyl-acetaldehyde. |
| 2,2-Dimethyl-thiazolidine | 80° C/8 | 1.5085 | 84% | 1440, 1360, 1115, 1060, 790 | Odour: meat-, pyridine-like, roasted, somewhat fatty. Flavour: pyrazine-like, somewhat meaty, slightly roasted, slightly bread-like. |
| 2-Propyl-thiazolidine | 55° C/0.3 | 1.5081 | 72% | 1460, 1190, 920, 810 | Odour: pungent, pyridine-like, harsh radish-like, slightly metallic. Flavour: pungent green, slightly caramellous note, towards bread. |
| 2-Phenyl thiazolidine | M.p. 109°–110° C | — | 90% | 1495, 1450, 1180, 825 | Odour: weakly greenish-leafy, earthy. Flavour: weakly greenish. |
| 2-Hexyl-thiazolidine | 65° C/0.08 | 1.4970 | 73% | 1455, 1190, 930, 820 | Odour: green, towards green beans, somewhat fatty note. Flavour: strongly green, towards beans, somewhat fatty. |
| 2-Ethyl-thiazolidine | 62°–63° C/11 | — | 88% | 1460, 1195, 915, 835, 780 | Odour: pyridine-ammonia like, strong, slightly nutty background. Flavour: slightly fruity, after-taste: leeks, mustard-like. |
| 2-Ethyl-2-methyl-thiazolidine | 50° C/0.07 | 1.5080 | 59% | 1460, 1440, 1375, 1120, 1090, 805, 775 | Odour: pungent, pyridine-like, towards fish, meat, camphorous background, woody. Flavour: ammonia-like. |
| 2-Ethyl-2-propyl-thiazolidine | 69°–70° C/0.01 | 1.5027 | 63% | 3320, 1460, 1375, 1115, 825 | Odour: spicy, slightly milky. |
| 2-Ethoxycarbonylmethyl-2-methyl-thiazolidine | 69°–72° C/0.02 | 1.5086 | 34% | 3340, 1730, 1610, 1445, 1370, 1175 | Odour: ester-like, sulphurous, green, somewhat spicy. |
| 2-(2-Ethoxycarbonylethyl)-2-methyl-thiazolidine | 101°–104° C/0.03 | 1.5038 | 54% | 3350, 1730, 1445, 1375, 1180, 800 | Odour: sulphurous, meat-like, sweetish. |
| 2-Methyl-2-nonyl-thiazolidine | 108°–112° C/0.03 | 1.4895 | 57% | 3320, 1465, 1375, 1135, 790, 730 | Odour: slightly fish and amine-like, tunny-like. |
| 2-Dimethoxymethyl-thiazolidine | 52°–55° C/0.01 | 1.5027 | 49% | 3340, 1440, 1375, 1105, 1090 | Odour: meat-like, slightly roasted. |
| 2-Decyl-thiazolidine | 115°–125° C/0.03 M.p. 25°–30° C | — | 14% | 3300, 1465, 805, 715 | Odour: woody earthy, quinoline-like. |
| 2-Acetoxymethyl-2-methyl-thiazolidine | 70°–72° C/0.02 | 1.5070 | 58% | 3350, 1740, 1450, 1380, 1235, 1035 | Odour: roasted, spicy, peanut-like. |
| 2-(1-Acetoxyethyl)-2-methyl-thiazolidine | 66°–70° C/0.02 | 1.5004 | 40% | 3350, 1740, 1445, 1370, 1240, 1055 | Odour: sulphurous, slightly burnt, kohlrabi. |
| 2,2-Bis(acetoxymethyl)-thiazolidine | 122°–123° C/0.03 | 1.5149 | 50% | 3350, 1740, 1440, 1375, 1235, 1015 | Odour: spicy, roasted, pyrazine-like, bread-like. Flavour: bread-like, somewhat burnt. |
| 2,2-Bis(ethoxycarbonyl)-thiazolidine | 115°–117° C/0.04 M.p. 31°–33° C | — | 45% | 3340, 1735, 1450, 1370, 1025 | Odour: sweet, fruity, somewhat burnt. |
| 2-(3-Hydroxypropyl)-2-methyl-thiazolidine | 109°–111° C/0.02 M.p. 23° C | 1.5290 | 56% | 3300, 1450, 1380, 1210, 1070 | Odour: roasted, burnt, sulphurous. |
| 2-(2,2-Dimethoxyethyl)-2-methyl-thiazolidine | 68°–71° C/0.02 | 1.4978 | 40% | 3360, 1445, 1375, 1125, 1050, 790 | Odour: spicy, meat-like, fatty, salami. |
| 2-Ethoxycarbonyl-2-(1-ethoxycarbonyl-ethyl)-thiazolidine | 105°–110° C/0.05 | 1.4902 | 29% | 3360, 1735, 1465, 1370, 1250, 1190, | Odour: roasted, peanut-like, bread-like. Flavour: bread-like. |
| 2-[2-(5-Methylthienyl)]-thiazolidine | M.p. 66°–67° C | | 31% | 1445, 839, 805 | Odour: spicy, green, slightly phenolic, celery-like. |

Table-continued

| Thiazolidine | B.p./mm Hg | $n_D^{20}$ | Yield | IR (cm$^{-1}$) | Olfactory interpretation |
|---|---|---|---|---|---|
| 2-[2-(5-Methylfuryl)]-thiazolidine | M.p. 46°–48° C | | 38% | 1456, 1178, 1160, 1023, 838 | Odour: mushroom-like, slightly roast. |
| 2-(2-Pyridyl)-thiazolidine | 123°–124° C/0.3 | | 54% | 1476, 1457, 1436, 1186, 1002, 833, 790 | Odour: woody, cedarwood-like, somewhat smoky, meaty, sausage-like. |
| 2,2-Bis(ethoxycarbonyl-methyl)-thiazolidine | 126°–134° C/0.06 | 1.4911 | 36% | 3350, 1735, 1470, 1370, 1180, 1030 | Odour: fatty, slightly greenish, salami-like, meaty. Flavour: slightly greenish, mushroom-like, meaty. |
| 2-(4-Methyl-3-pentenyl)-thiazolidine | 58°–62° C/0.01 | 1.5209 | 47% | 3300, 1670, 1450, 1380, 830 | Odour: green, amine-like, vegetable-like, slightly flowery. |
| 2-[4-(2,2-Dimethyl-dioxolanyl)]-thiazolidine | 84°–87° C/0.02 | 1.5128 | 75% | 3340, 1475, 1375, 1210, 1070, 850 | Odour: sardine-like, slightly roasted. Flavour: nutty-earthy, towards peanuts. |
| 2-(2-Thienyl)-thiazolidine | 106°–107° C/0.35 M.p. 44°–46° C | | 47% | 1450, 1235, 1195, 1180, 929, 857, 833 | Odour: spicy, slightly sulphurous, smoky. Flavour: smoky, phenolic. |
| 2-[2-(N-methyl-pyrrolyl)]-thiazolidine | 105°–106° C/0.2 | | 50% | 1495, 1448, 1300, 1193, 848, 790 | Odour: slightly metallic, fatty. |

The following Examples illustrate typical odorant and/or flavouring compositions provided by the invention:

Example A

| Composition (Smoke Aroma) | A | B |
|---|---|---|
| | Parts by Weight | |
| Methylisoeugenol | 0.5 | 0.5 |
| Pyruvic acid | 3.0 | 3.0 |
| Heliotropin | 3.0 | 3.0 |
| Furfurol | 5.0 | 5.0 |
| Eugenol | 5.0 | 5.0 |
| Vanillin | 9.0 | 9.0 |
| Guaiacol | 20.0 | 10.0 |
| 2,2-Pentamethylene-thiazolidine | — | 10.0 |
| Alcohol | 954.5 | 954.5 |
| | 1000.0 | 1000.0 |

The partial replacement of guaiacol in aroma composition A by 2,2-pentamethylene-thiazolidine gives a more typical smoky note.

Example B

| Composition (Licorice Aroma) | A | B |
|---|---|---|
| | Parts by Weight | |
| Dimethylresorcin (10% alcohol) | 2.0 | 2.0 |
| Isobutylquinoline (10% alcohol) | 5.0 | 5.0 |
| Mousse de Chene (10% alcohol) | 10.0 | 10.0 |
| Corylone | 30.0 | 30.0 |
| Methylionone | 60.0 | 60.0 |
| Maltol | 10.0 | 10.0 |
| Anethol synth. | 160.0 | 100.0 |
| 2,2-Dimethylthiazolidine | — | 60.0 |
| Alcohol | 723.0 | 723.0 |
| | 1000.0 | 1000.0 |

The partial replacement of Anethol synth. in aroma composition A by 2,2-dimethylthiazolidine gives a slightly greenish, nut-like note which is strongly reminiscent of licorice.

Example C

| Composition (Hazelnut Aroma) | A | B | C |
|---|---|---|---|
| | Parts by weight | | |
| Maltol | 2.0 | 2.0 | 2.0 |
| Acetylmethylcarbinol | 2.0 | 2.0 | 2.0 |
| Acetophenone | 3.0 | 3.0 | 3.0 |
| Acetanisole | 3.0 | 3.0 | 3.0 |
| Furfurylmercaptan | 5.0 | 5.0 | 5.0 |
| Cinnamic acid amyl ester (10% in alcohol) | 5.0 | 5.0 | 5.0 |
| Vanillin | 10.0 | 10.0 | 10.0 |
| Diacetyl (10% in alcohol) | 10.0 | 10.0 | 10.0 |
| Aldehyde C 18 | 10.0 | 10.0 | 10.0 |
| Phenylacetic acid amyl ester (10% in alcohol) | 10.0 | 10.0 | 10.0 |
| Phenylacetaldehyde | 10.0 | 10.0 | 10.0 |
| Corylone | 15.0 | 15.0 | 15.0 |
| Benzaldehyde | 100.0 | 100.0 | 100.0 |
| Dimethylresorcinol | 350.0 | 300.0 | 270.0 |
| 2-Acetyl-2-ethyl-thiazolidine/ 2-methyl-2-propionyl-thiazolidine mixture | — | 50.0 | — |
| 2-Ethoxycarbonyl-2-methyl-thiazolidine | — | — | 80.0 |
| Alcohol | 465.0 | 465.0 | 465.0 |
| | 1000.0 | 1000.0 | 1000.0 |

The partial replacement of dimethylresorcinol in aroma composition A by a 2-acetyl-2-ethyl-thiazolidine/2-methyl-2-propionyl-thiazolidine mixture or by 2-ethoxycarbonyl-2-methyl-thiazolidine gives a nut-like note which is strongly reminiscent of hazelnut.

Example D

| Composition (Bean Aroma) | A | B | C |
|---|---|---|---|
| | \multicolumn{3}{c}{Parts by Weight} | | |
| Methylchavicol (1% in alcohol) | 0.5 | 0.5 | 0.5 |
| Garlic (1% in alcohol) | 2.0 | 2.0 | 2.0 |
| Thymol (1% in alcohol) | 0.5 | 0.5 | 0.5 |
| Isobutyric acid piperonyl ester (1% in alcohol) | 3.0 | 3.0 | 3.0 |
| Nona-2,6-dienal (1% in alcohol) | 5.0 | 5.0 | 5.0 |
| Acetic acid linalyl ester (1% in alcohol) | 5.0 | 5.0 | 5.0 |
| 3-Hexenyl-acetylacetate | 10.0 | 10.0 | 10.0 |
| 2-(2-Methylthioethyl)-thiazolidine | — | 1.0 | — |
| 2-Pentylthiazolidine | — | — | 0.5 |
| Alcohol | 974.0 | 973.0 | 973.5 |
| | 1000.0 | 1000.0 | 1000.0 |

The addition of 2-(2-methylthioethyl)-thiazolidine and/or 2-pentylthiazolidine to aroma composition A gives an intense vegetable-like note which is reminiscent of beans.

We claim:
1. 2-Methyl-2-(4-methyl-3-penten-1-yl)-thiazolidine.

* * * * *